United States Patent
Owczarczyk

(10) Patent No.: US 6,903,214 B1
(45) Date of Patent: Jun. 7, 2005

(54) SYNTHESIS OF BIS(AZINYL)AMINE-BF$_2$ COMPLEX

(75) Inventor: Zbyslaw R. Owczarczyk, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/733,086

(22) Filed: Dec. 11, 2003

(51) Int. Cl.$^7$ ................................................ C07F 5/02
(52) U.S. Cl. ............................................................... 546/13
(58) Field of Search ............................................ 546/13

(56) References Cited

PUBLICATIONS

B. P. Hoag et al, "Organic Element for Electroluminescent Devices", U.S. Appl. No. 10/086,085 filed Feb. 28, 2002 (D–83723).

B. P. Hoag et al, "Organic Element for Electroluminescent Devices", U.S. Appl. No. 10/183,242 filed Jun. 27, 2002 (D–83723 A) (CIP of U.S. Appl. No. 10/086,085).

G. Sathyamoorthi et al, Heteroatom Chemistry 1993, vol. 4, No. 6, pp. 603–608.

*Primary Examiner*—Johann Richter
*Assistant Examiner*—Chukwuma Nwaonicha
(74) *Attorney, Agent, or Firm*—Arthur E. Kluegel

(57) ABSTRACT

Disclosed is a process of forming a bis(azinyl)amine-BF$_2$ complex, where a boron atom is complexed by two ring nitrogens of a deprotonated bis(azinyl)amine compound, comprising the step of reacting BF$_3$ with a protonated bis(azinyl)amine in the presence of a polar aprotic organic solvent that is not reactive with the BF$_3$ under reaction conditions. Such process provides good yields, even when a bulky group is present on the bis(azinyl)amine compound.

17 Claims, No Drawings

SYNTHESIS OF BIS(AZINYL)AMINE-BF₂ COMPLEX

FIELD OF THE INVENTION

This invention relates to the field of organic synthesis and to a process of forming a bis(azinyl)amine-BF₂ complex, where the boron atom is complexed by two ring nitrogens of a deprotonated bis(azinyl)amine compound, comprising reacting BF₃ with a protonated bis(azinyl)amine compound in the presence of polar aprotic organic solvent that is not reactive with the BF₃ under reaction conditions.

BACKGROUND OF THE INVENTION

Electroluminescent devices are well-known for their utility in providing light emissions. Among the emitting materials useful in such devices are bis(azinyl)amine-BF₂ complex, where the boron atom is complexed by two ring nitrogens of a deprotonated bis(azinyl)amine compound. Pending and commonly assigned U.S. Ser. No. 10/183,242, filed Jun. 27, 2002 CIP of U.S. Ser. No. 10/086,085 filed Feb. 28, 2002 teaches a method of preparing bis(azinyl)amine-BF₂ complexes by reacting BF₃ with a protonated bis(azinyl)amine compound in toluene as an organic solvent. Sathyamoorthi et al. (*Heteroatom Chemistry* 1993, 6, 603) describes the synthesis bis(azinyl)amine-BF₂ complex using toluene and dichloromethane as an organic solvent. While these methods produced the desired product generally in satisfactory yield, they gave low yield, typically below 5%, when the selected deprotonated bis(azinyl)amine compound was substituted with bulky groups such as phenyl, t-butyl or mesityl groups.

It is a problem to be solved to provide an efficient process for the synthesis of bis(azinyl)amine-BF₂ complexes, especially those with bulky substituents.

SUMMARY OF THE INVENTION

The invention provides a process of forming a bis(azinyl)amine-BF₂ complex, where a boron atom is complexed by two ring nitrogens of a deprotonated bis(azinyl)amine compound, comprising the step of reacting BF₃ with a protonated bis(azinyl)amine in the presence of a polar aprotic organic solvent that is not reactive with the BF₃ under reaction conditions.

Such process provides good yields, even when a bulky group is present on the bis(azinyl)amine compound.

DETAILED DESCRIPTION OF THE INVENTION

The detailed invention is summarized above. The process enables synthesis of bis(azinyl)amine-BF₂ complexes by reacting a protonated bis(azinyl)amine compound with BF₃ or a BF₃ source in high yield. The phrase protonated means that at least one nitrogen atom of the compound is substituted with a hydrogen atom.

The protonated bis(azinyl)amine reactant compound may be usefully represented by Formula (1):

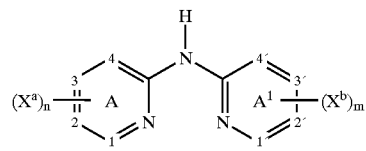

wherein

A and A' represent independent azine ring systems corresponding to 6-membered aromatic ring systems containing at least one nitrogen;

each $X^a$ and $X^b$ is an independently selected substituent, two of which may join to form a fused ring to A or A', and m and n are independently 0 to 4; and atoms 1, 2, 3, 4, 1', 2', 3', and 4' are independently selected as either carbon or nitrogen atoms.

The compound represented by Formula 1 is reacted with either BF₃ or BF₃ source, for example Et₂O— BF₃. Other BF₃ sources include but are not limited to Me₂O— BF₃, THF— BF₃, Me₂S— BF₃. The amount of BF₃ used in this process, relative to the starting material as per formula (1), can range from 1–50 equivalents.

The resulting product of this process is depicted by Formula (2):

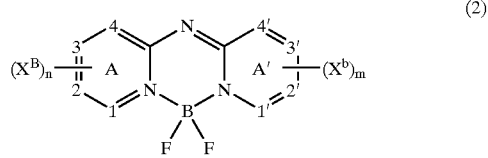

wherein the substituents and variables are as described for Formula (1).

The reaction is carried out in the presence of a polar aprotic solvent that is not reactive with BF₃ under the reaction conditions. Conveniently it is a polar aprotic organic solvent containing a nitrile group is conveniently one represented by formula (3)

wherein:

$R_1$, $R_2$ and $R_3$ each independently represents hydrogen, fluorine, alkyl, aryl, alkoxy, aryloxy, dialkylamino, diarylamino, cyano, or nitro groups; and $R_1$ and $R_2$, $R_2$ and $R_3$ or $R_1$ and $R_3$ may join to form a cycloalyl or an aryl ring group.

Typical substituents include alkyl, aryl alkoxy, aryloxy, dialkylamino, diarylamino, cyano, or nitro groups. The various alkyl groups, such as perfluoroalkyl groups, typically contain 1 to 6 carbon atoms, but less than 12 carbon atoms. The cycloalkyl moieties usually contain from 3 to 10 carbon atoms, but typically contain five or six carbon atoms—e.g., cyclopentyl or cyclohexyl structure. The aryl groups are usually phenyl moieties.

The process of the invention is exemplified in the following scheme, to prepare Inv-7:

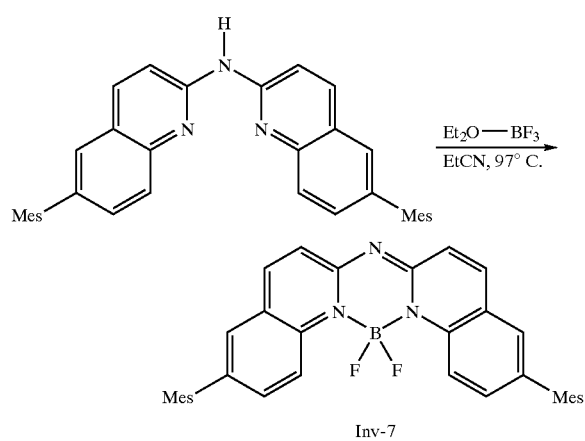
Mes = mesityl
Illustrative examples of boron compounds complexed by two ring nitrogens of a deprotonated bis(azinyl)amine compound that can be prepared using the present invention are the following:
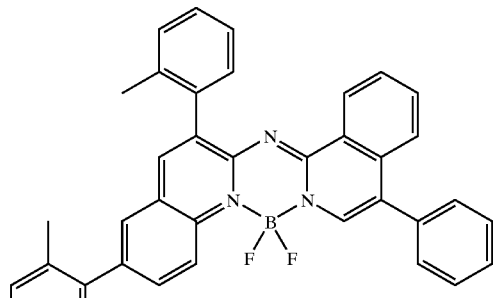
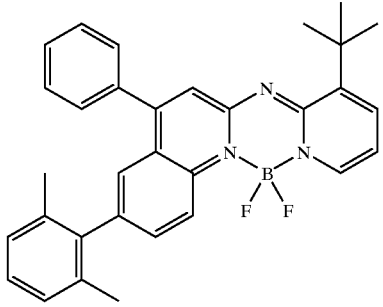
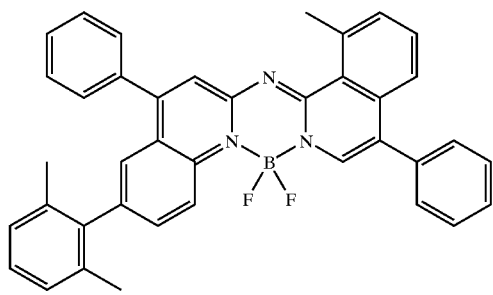
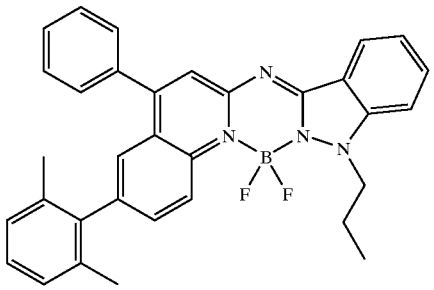
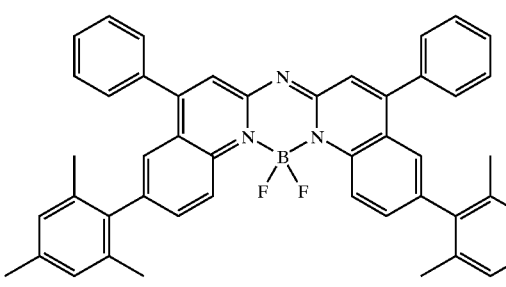
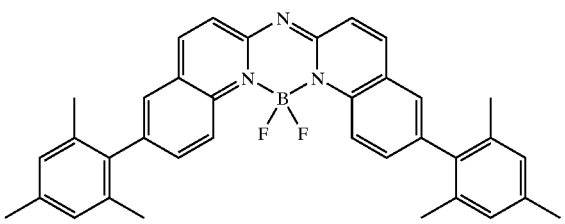
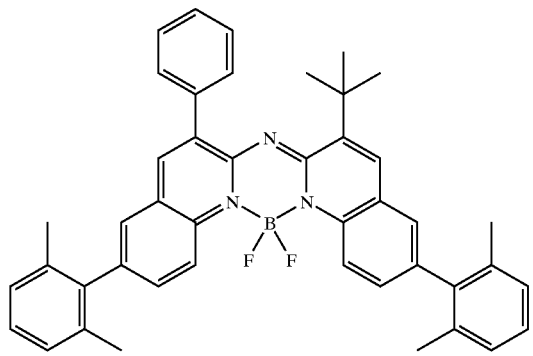
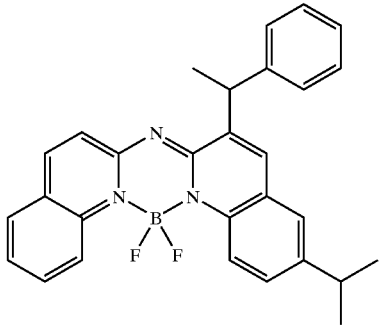

-continued

Inv-9
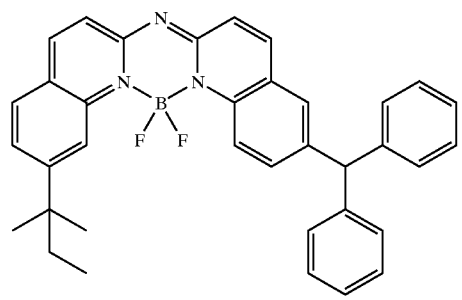

Inv-10
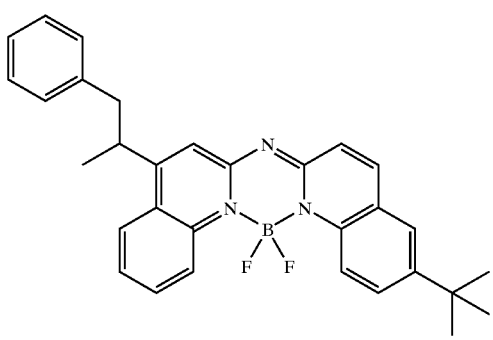

Inv-11
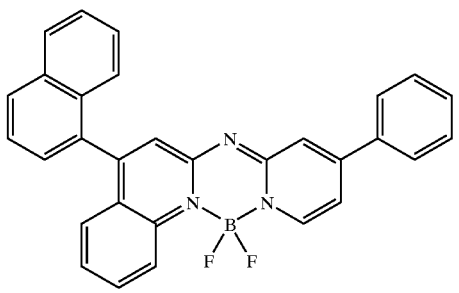

Inv-12
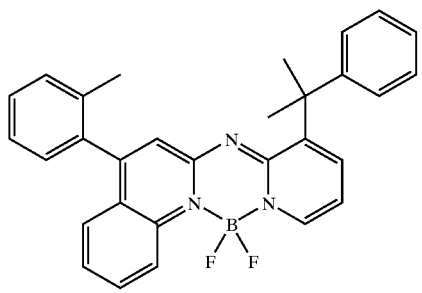

Inv-13
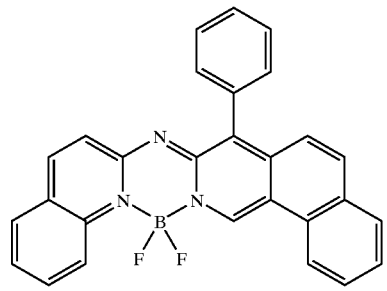

-continued

Inv-14
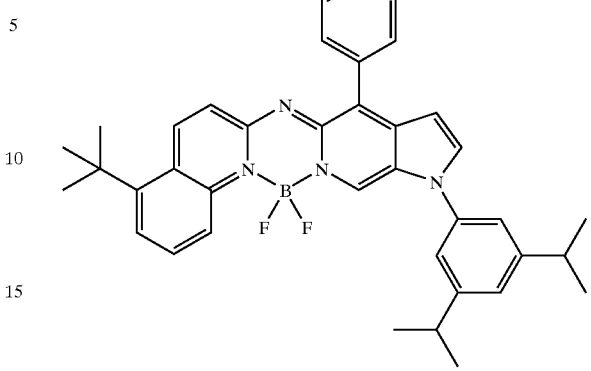

Under the reaction conditions stated above, the temperature needed to effect the formation of the complex depicted in formula (2), is typically room temperature (18° C.) to 200° C. Conveniently the reaction is carried out at temperature of at least 80° C. The temperature requirements can be also dictated by the nature of the substituents described in Formulas (1) and (2) and the solubility of the starting ligand (1).

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, cyclohexyl, 3-(2,4-di-t-pentylphenoxy)propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonyl amino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur, phosphorous, or boron, such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

EXAMPLES

Example 1

2 L 4-necked flask equipped with sealed mechanical stirrer, thermometer, and reflux condenser, dropping funnel and nitrogen inlet was charged with compound 7 (130.00 g, 256 mmol) and dry propionitrile (1000 ml). $BF_3Et_2O$ (156 ml, 1250 mmol) was added from the funnel, after 1 hour the reaction mixture was warmed about 97° C. and refluxed for 36 hours. Before the reaction mixture was cooled to RT about half of propionitrile was removed by fast distillation. The cool concentrated reaction mixture was slowly (over 20–30 minutes) added to water (10 L) at 18–28° C. The water mixture was stirred (1–3 h) to solidified product which was isolated by filtration, washed with water (400 ml), saturated sodium bicarbonate (400 ml), water (3×400 ml) and dried with flow of air for 3 hours. The crude product was transferred to flask, slurry with i-$Pr_2O$ (600 mL), stirred for 0.5 h, filtered off, washed with $Et_2O$ (250 mL) and dried with flow of air for 1–2 h and then in vacuum oven at 70° C. for 6–12 hours to yield 119.6 g (83%) of the desire product—Inv 7.

Examples 2, 3

These were synthesized in the same manner as Example 1 except solvent and temperature selection as indicated in the table.

Examples 4–6

The protonated starting compound 7(1.30 g, 2.56 mmol), 10 ml of an appropriate dry solvent (tetrahydrofuran, toluene or dichloromethane) and $BF_3Et_2O$ (1.56 ml, 12.50 mmol) were combined in a sealed bottle and heated at the temperature indicated in the Table 1.

The progress of the reactions was monitored by TLC and LC analysis.

Table 1 summarizes the examples including the reaction conditions applied in the synthesis of bis(azinyl)amine-$BF_2$ complex from deprotonated bis(azinyl)amine compound in different solvents and resulting yields. The yields are based on protonated compound starting material.

TABLE 1

Illustrative Examples for Making, Inv-7 (36 hrs)

| Example | Type | Solvent | Temp. | Yield |
|---|---|---|---|---|
| 1 | Inventive | propionitrile | 97° C. | 83% |
| 2 | Inventive | acetonitrile | 80° C. | 79% |
| 3 | Inventive | butyronitrile | 115° C. | 91% |
| 4 | Comparative | toluene | 115° C. | 4% |
| 5 | Comparative | tetrahydrofuran | 65° C. | <1% |
| 6 | Comparative | dichloroethane | 65° C. | <1% |

Table 1 shows that, for the samples tested, the yields using innovative process range from 70–91% yield, while those for the comparative process ranged from 0–4%. Poor results with bulky substituents wee also observed with solvents such as DMSO and DMF.

The entire contents of the patents and other publications referred to in this specification are incorporated herein by reference.

What is claimed is:

1. A process of forming a 2-2' bis(pyridyl)amine-$BF_2$ complex, where a boron atom is complexed by two ring nitrogens, comprising the step of reacting $BF_3$ with an amine having Formula (1)

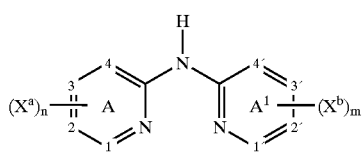

(1)

wherein:
  A and A' represent independent azine ring systems corresponding to 6-membered aromatic ring systems containing at least one nitrogen;
  each $X^a$ and $X^b$ is an independently selected substituent, two of which may join to form a fused ring to A or A';
  m and n are independently 0 to 4; and
  atoms 1, 2, 3, 4, 1', 2', 3', and 4' are carbon atoms;
in the presence of a polar aprotic organic solvent containing a nitrile group that is not reactive with the $BF_3$ under reaction conditions and has the Formula:

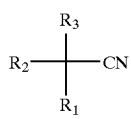

(3)

wherein
  $R_1$, $R_2$ and $R_3$ each independently resents hydrogen, fluorine, alkyl, aryl, alkoxy, aryloxy, dialkylamino, diarylamino, cyano, or nitro groups wherein at least one of $R_1$, $R_2$ and $R_3$ is not H; and
  $R_1$ and $R_2$, $R_2$ and $R_3$ or $R_1$ and $R_3$ may join to form a cycloalkyl or an aryl ring group.

2. The process of claim 1 wherein at least two of $R_1$, $R_2$ and $R_3$ are not H.

3. The process of claim 1 wherein $R_1$ and $R_2$ represent H and $R_3$ represents a methyl group.

4. The process of claim 1 wherein $R_1$ and $R_2$ represent H and $R_3$ represents an ethyl group.

5. The process of claim 1 wherein at least two of $R_1$, $R_2$ and $R_3$ are H.

6. The process of claim 1 wherein the $BF_3$ source is selected from the group consisting of $BF_3$ gas, $BF_3$ solution in an organic solvent or $BF_3$ complex with organic solvent or compound.

7. The process of claim 1 wherein the $BF_3$ source is selected from the group consisting of $BF_3$ complexed with diethyl ether, dimethyl ether or tetrahydrofuran.

8. The process of claim 1 wherein $BF_3$ is used in the amount 1–50 equivalents per mol of the amine compound having Formula (1).

9. The process of claim 1 wherein the reaction is performed at a temperature of at least 18° C.

10. The process of claim 1 wherein the reaction is performed at a temperature of at least 80° C.

11. The process of claim 1 wherein the reaction is performed at a temperature of at least 115° C.

12. The process of claim 1 where at least one $X^a$ or $X^b$ is present containing 4 or more carbon atoms.

13. The process of claim 12 wherein the $X^a$ or $X^b$ group is selected from the group consisting of phenyl and t-butyl groups.

14. The process of claim 13 wherein the $X^a$ or $X^b$ group is a phenyl group.

15. The process of claim 13 wherein the $X^a$ or $X^b$ group is a phenyl group containing at least one methyl group substituent.

16. The process of claim 13 wherein the $X^a$ or $X^b$ group is a mesityl group.

17. The process of claim 1 wherein the amine-$BF_2$ complex is selected from the following:

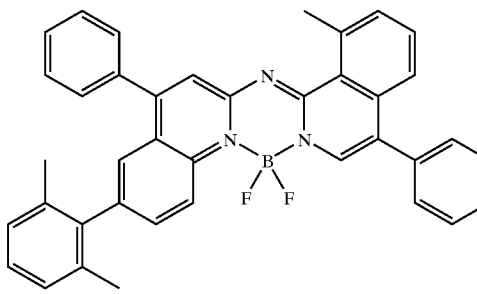

Inv-1

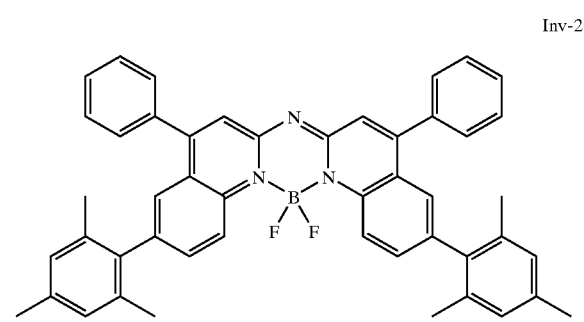

Inv-2

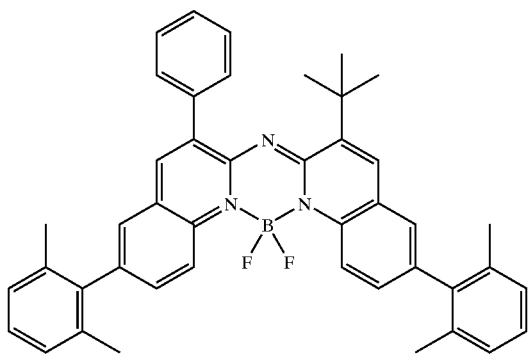

Inv-3

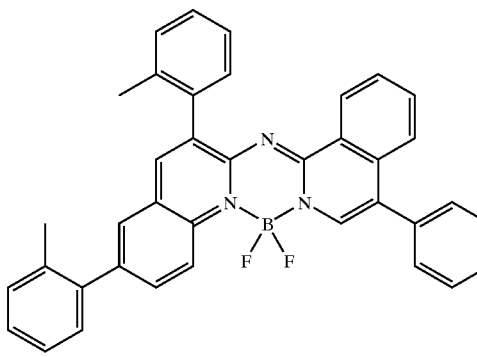

Inv-4

-continued
Inv-5
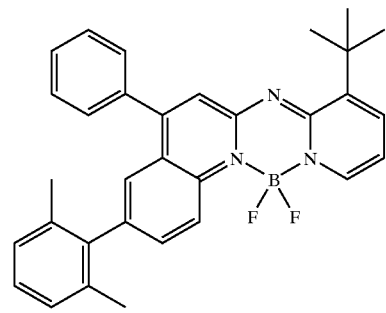
Inv-7
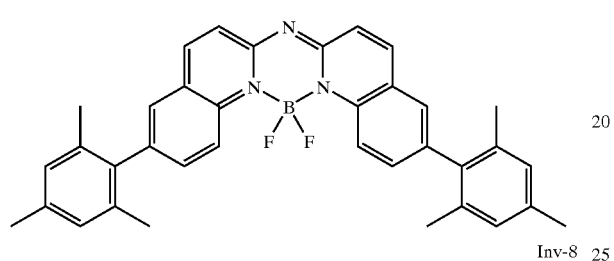
Inv-8
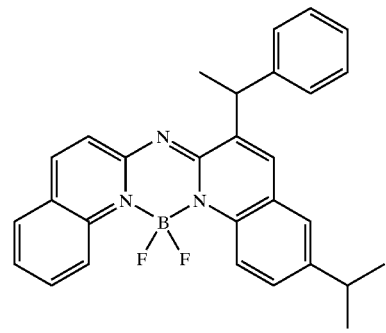
Inv-9
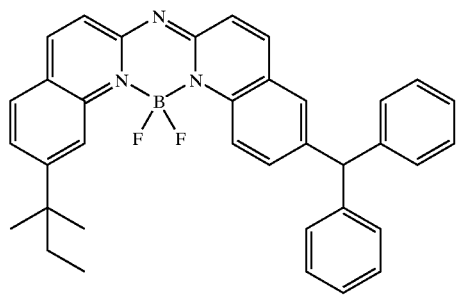
Inv-10
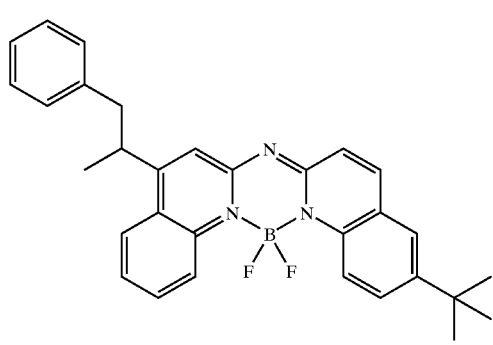
-continued
Inv-11
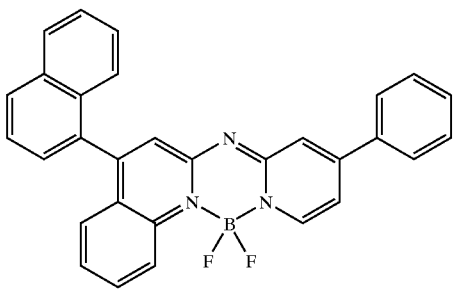
Inv-12
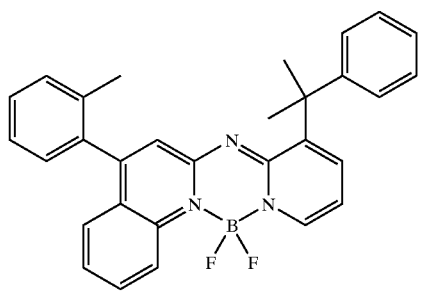
Inv-13
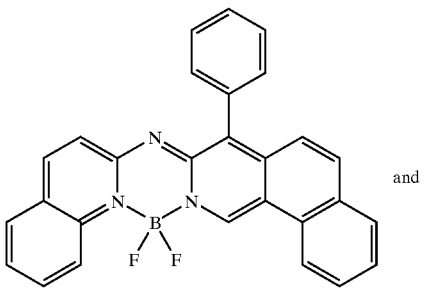
and
Inv-14
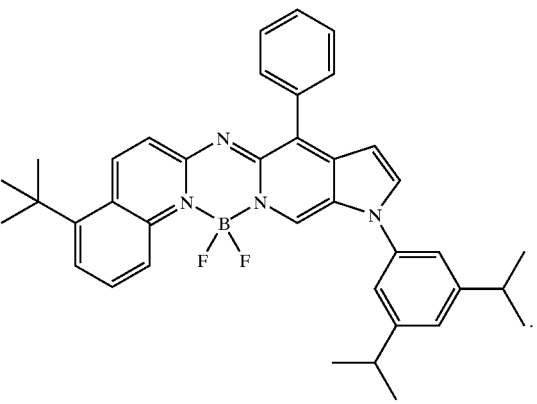
* * * * *